United States Patent
Chen (10) Patent No.: US 12,357,430 B2
(45) Date of Patent: Jul. 15, 2025

(54) ORTHOPEDIC IMPLANT THAT SAVES BONE CUTTING WITH DRILL BITS IN ADVANCE IN ORTHOPEDIC AND DENTAL SURGERIES

(71) Applicant: STAR GENERATION LIMITED, New Taipei (TW)

(72) Inventor: Chun-Leon Chen, Taipei (TW)

(73) Assignee: STAR GENERATION LIMITED, New Taipei (TW)

( * ) Notice: Subject to any disclaimer, the term of this patent is extended or adjusted under 35 U.S.C. 154(b) by 389 days.

(21) Appl. No.: 17/970,841

(22) Filed: Oct. 21, 2022

(65) Prior Publication Data
US 2023/0190418 A1  Jun. 22, 2023

(30) Foreign Application Priority Data
Dec. 16, 2021  (TW) .................................. 110147276

(51) Int. Cl.
*A61C 8/00*  (2006.01)
*A61B 17/86*  (2006.01)

(52) U.S. Cl.
CPC .......... *A61C 8/0024* (2013.01); *A61B 17/863* (2013.01); *A61C 8/0045* (2013.01)

(58) Field of Classification Search
CPC .... A61C 8/0045; A61C 8/0024; A61B 17/863
See application file for complete search history.

(56) References Cited

U.S. PATENT DOCUMENTS

| | | | | |
|---|---|---|---|---|
| 2,382,019 A | * | 8/1945 | Miller | F16B 25/0073 411/386 |
| 5,199,873 A | * | 4/1993 | Schulte | A61C 8/0018 433/173 |
| 5,259,398 A | * | 11/1993 | Vrespa | A61C 8/0089 411/413 |
| 6,086,303 A | * | 7/2000 | Fluckiger | F16B 5/0275 411/399 |
| 6,203,324 B1 | * | 3/2001 | Wils | A61C 8/0089 433/221 |
| 6,585,740 B2 | * | 7/2003 | Schlapfer | A61B 17/8635 411/401 |

(Continued)

FOREIGN PATENT DOCUMENTS

DE  102006013456 A  * 9/2007

*Primary Examiner* — Ralph A Lewis
(74) *Attorney, Agent, or Firm* — Rabin & Berdo, P.C.

(57) ABSTRACT

An orthopedic implant includes a main body, which has a downward tapered configuration formed of a plurality of steps of different diametrical sizes arranged along a drilling axis, each of the steps includes a cylindrical and a conical section, and the conical section of the lowest and diametrically smallest step is downward tapered into an apex; an external thread, which is externally formed on the main body to cover all the cylindrical sections but not the conical sections; a plurality of lateral cutting flutes, which are formed on the external thread into the main body and extended from the apex to the diametrically largest step with a spacing distance left between upper ends of the lateral cutting flutes and a top of the largest step. The orthopedic implant can be independently driven into a bone without the need of bone cutting using drill bits in advance and enables good osseointegration.

9 Claims, 8 Drawing Sheets

(56) References Cited

U.S. PATENT DOCUMENTS

| | | | |
|---|---|---|---|
| 2008/0160483 A1* | 7/2008 | Danger | A61C 8/0012 433/174 |
| 2012/0225407 A1* | 9/2012 | Chen | A61C 8/0037 433/174 |
| 2015/0297321 A1* | 10/2015 | Chen | A61C 8/0025 433/174 |
| 2016/0220334 A1* | 8/2016 | Chen | A61C 8/0092 |
| 2023/0190418 A1* | 6/2023 | Chen | A61B 17/8635 433/174 |

* cited by examiner

ORTHOPEDIC IMPLANT THAT SAVES BONE CUTTING WITH DRILL BITS IN ADVANCE IN ORTHOPEDIC AND DENTAL SURGERIES

FIELD OF THE INVENTION

The present invention relates to an orthopedic implant that can be driven into a bone without the need of bone cutting using drill bits in advance, and more particularly, to an orthopedic implant that can be directly driven into a bone and allows good osseointegration.

BACKGROUND OF THE INVENTION

In treatment of a fractured bone, bone nails and fixation plates are usually used to fix the fractured bone in place. However, the bone nails and fixation plates tend to produce a stress when a patient moves his or her body. Therefore, bone nails and fixation plates are usually made of stainless steel or titanium alloys. Tests have proven the currently available materials for making bone nails and fixation plates have good biocompatibility. And, in a dental implant surgery, a dental implant made of titanium metal or zirconium dioxide can be implanted into a patient's alveolar bone to serve as an artificial tooth root functionally similar to the patient's original tooth. After the dental implant is tightly integrated with the alveolar bone, an artificial crown is formed on the titanium or zirconium dioxide dental implant to restore good appearance and chewing function of the patient's teeth.

However, when using the bone nails or the fixation plates to treat the fractured bone, or using the artificial tooth roots as dental implants, a surgeon or a dentist has to drill holes into the bone in the implant surgery before the bone nails and the fixation plates or the dental implants can be placed in the bone. To drill the bone, the surgeon or the dentist first evaluates the patient's bone or teeth condition and the required implant size, and determines the depth of hole to be drilled. The depth of drilled hole has an influence on the stability of implant placement. It is necessary to watch the drilled depth carefully during drilling to avoid improper implant placement. The bone drilling would increase the surgical time, chance of inflection, risk of heavy bleeding, patient's discomfort, and post-surgery complication. Further, a large quantity of strain energy, friction energy, and heat energy would be generated during bone drilling to destruct the material of the bone being drilled; and the energy produced in the process of bone drilling might have an influence on the rate of successful osseointegration.

SUMMARY OF THE INVENTION

A primary object of the present invention is to provide an orthopedic implant, which can be directly threaded into a bone and located in place in an orthopedic surgery or a dental implant surgery, so that a surgeon or a dentist can save the additional procedure of cutting bone with drill bits in advance. The orthopedic implant ensures optimal osseointegration and shortens the overall surgical time needed for the orthopedic or the dental implant surgery to thereby reduce the possibility of infection and the risk of heavy bleeding.

Another object of the present invention is to provide an orthopedic implant that has a special contour design with specific ratio of cutting flute overall volume to implant main body volume, so as to prevent the orthopedic implant from creating lateral stress to cause broken and collapsed bone under pressure; and the orthopedic implant can also reduce the condition of overheated bone and resultant necrosis.

A further object of the present invention is to provide an orthopedic implant that includes at least one set of lateral cutting blade edges, so that the orthopedic implant can not only drill the bone in a straight linear direction, but also cut the bone laterally while being driven into the bone.

A still further object of the present invention is to provide an orthopedic implant that has partial areas subjected surface treatment to largely enhance good osseointegration in subsequent bone healing process.

To achieve the above and other objects, the orthopedic implant according to the present invention includes a main body, an external thread, and a plurality of lateral cutting flutes. The main body is formed with a plurality of steps arranged along a drilling axis and having diametrical sizes gradually increased from bottom to top, so as to have a stepped and downward tapered overall configuration. Each of the steps includes a cylindrical section and a conical section providing a drilling surface, and the conical section of the step having the smallest diametrical size is downward extended and tapered to form an apex. The external thread is formed on an outer surface of the main body to cover all cylindrical sections on the main body, while the conical sections on the main body are exposed to an outer environment without being covered by the external thread. The lateral cutting flutes are formed on the external thread and sunken into the main body. Each of the lateral cutting flutes is extended from the apex located at a lower end of the main body to the step having the largest diametrical size and located around an upper end of the main body, while a spacing distance is formed between an upper end of the lateral cutting flute and the upper end of the main body.

In a preferred embodiment, the orthopedic implant includes more than one lateral cutting structure design, one of which is formed by providing oblique recessed sections on a side of each of the lateral cutting flutes is formed a plurality of oblique recessed portions corresponding to the cylindrical sections, such that each of the cylindrical sections has an obliquely cutting blade edge; and an acute angle is formed between the obliquely cutting blade edge and the conical section located at the same step.

Another lateral cutting structure design is a plurality of lateral cutting members formed on the apex. Each of the lateral cutting members has a laterally cutting blade edge correspondingly located adjacent to one of the lateral cutting flutes. A length of each lateral cutting flute corresponding to the apex has a width that is gradually reduced from an end of the apex located adjacent to the cylindrical section of the diametrically smallest step toward a tip of the apex.

At least one of the external thread and the lateral cutting flutes is subjected to surface treatment to form a coarse surface. A depth of the lateral cutting flutes on the steps starts from a pitch circle of the external thread to extend into the main body to a location close to the drilling axis, such that a ratio of an overall volume of all the lateral cutting flutes on the main body to a volume of the main body is ranged between 0.45:1 and 0.55:1.

In an operable embodiment, the main body further includes a sealing section located adjacent to the diametrically largest step; and the sealing section is provided on an outer circumferential surface with a sealing thread, the sealing thread has an outmost diameter larger than a step diameter defined by the external thread on a circumferential surface of the diametrically largest step.

The sealing section is provided at a top center with an engagement portion, and a rotary tool is correspondingly detachably mounted to the engagement portion for rotating the orthopedic implant about the drilling axis, and the apex and the drilling surfaces provided by the conical sections can be driven into the bone linearly to destruct the bone, allowing the whole orthopedic implant to move into the bone. An abutment can be fixedly connected to the engagement portion and exposed from an alveolar bone when the orthopedic implant is applied in dentistry.

The present invention is characterized in that the apex formed at the bottom of the orthopedic implant and the conical sections formed at the bottom of all steps together drill a hole into the bone gradually, so that the hole formed on the bone is gradually expanded from a size corresponding to the diametrically smallest step to a size corresponding to the diametrically largest step, allowing the orthopedic implant to drill downward quickly like a drill bit. And, since the external thread provides the same pitch on two diametrically opposite sides of each of the steps, the orthopedic implant can tightly engage with the bone to achieve good locating effect.

Further, with blade edges for lateral cutting being formed on the cylindrical sections of the steps and on the apex, the orthopedic implant being wrongly implanted into the bone in a skewed direction in the implantation surgery can be shifted to cut the bone laterally and accordingly, adjusted to the correct position. Therefore, the risk of failure in the implanting surgery can be reduced.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
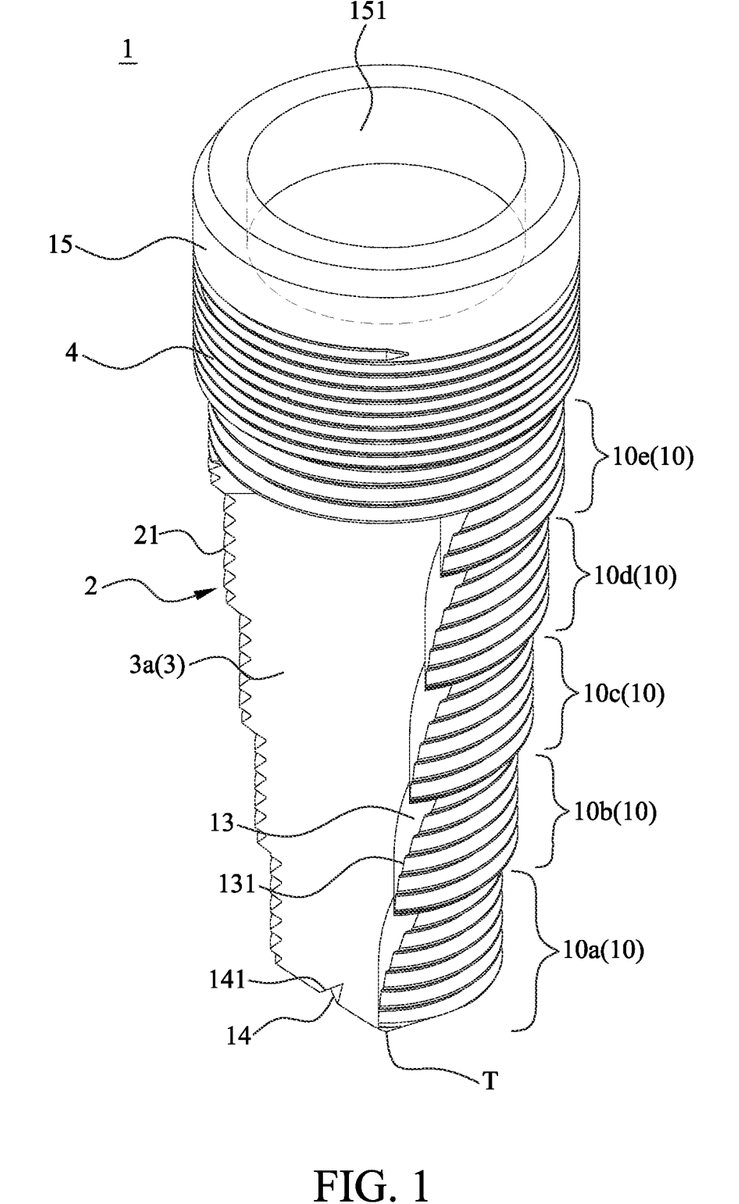
FIG. 1 is a perspective view of an orthopedic implant according to a first embodiment of the present invention.
Figure 2:
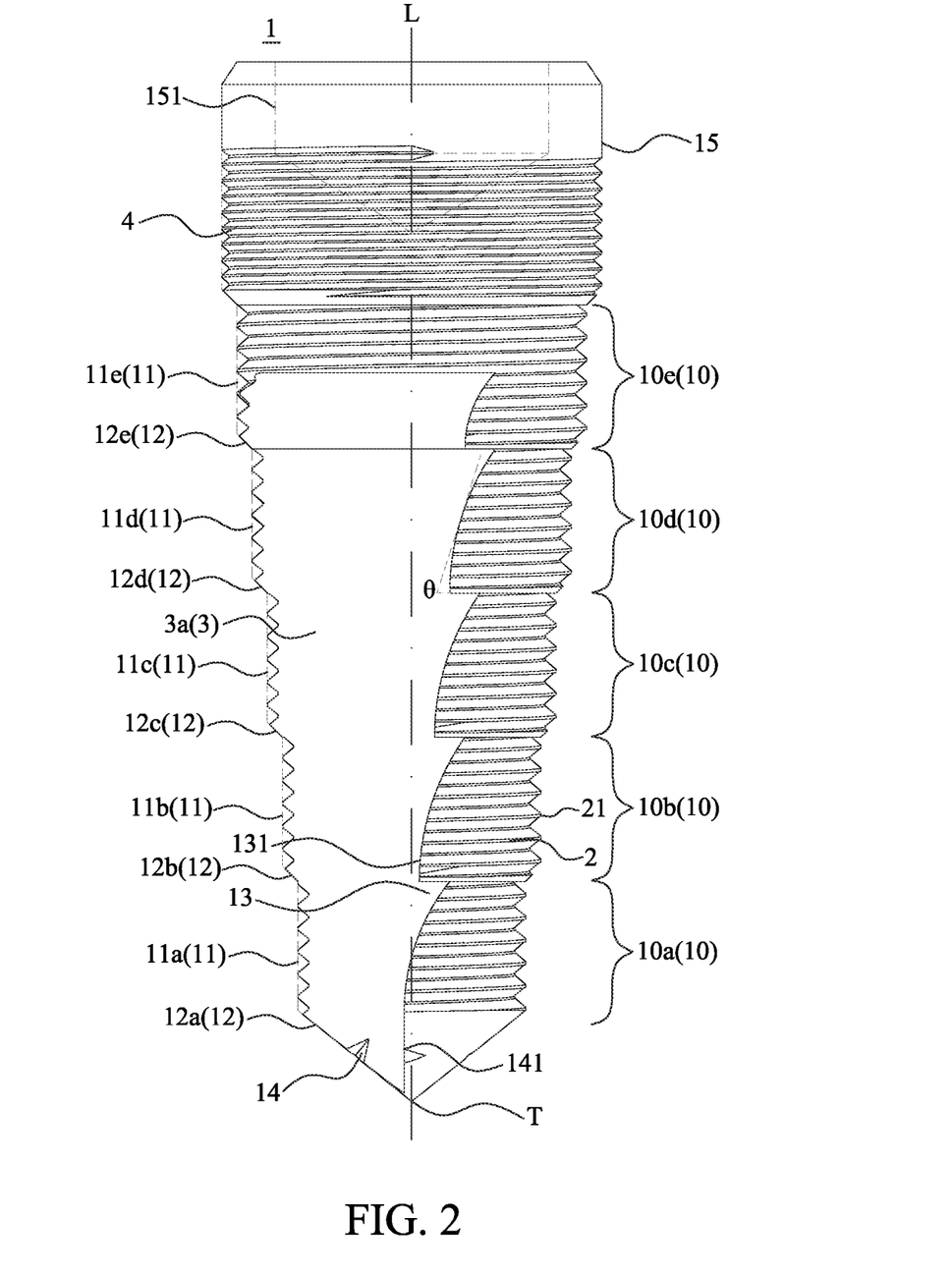
FIG. 2 is a side view of the orthopedic implant of FIG. 1.
Figure 3:
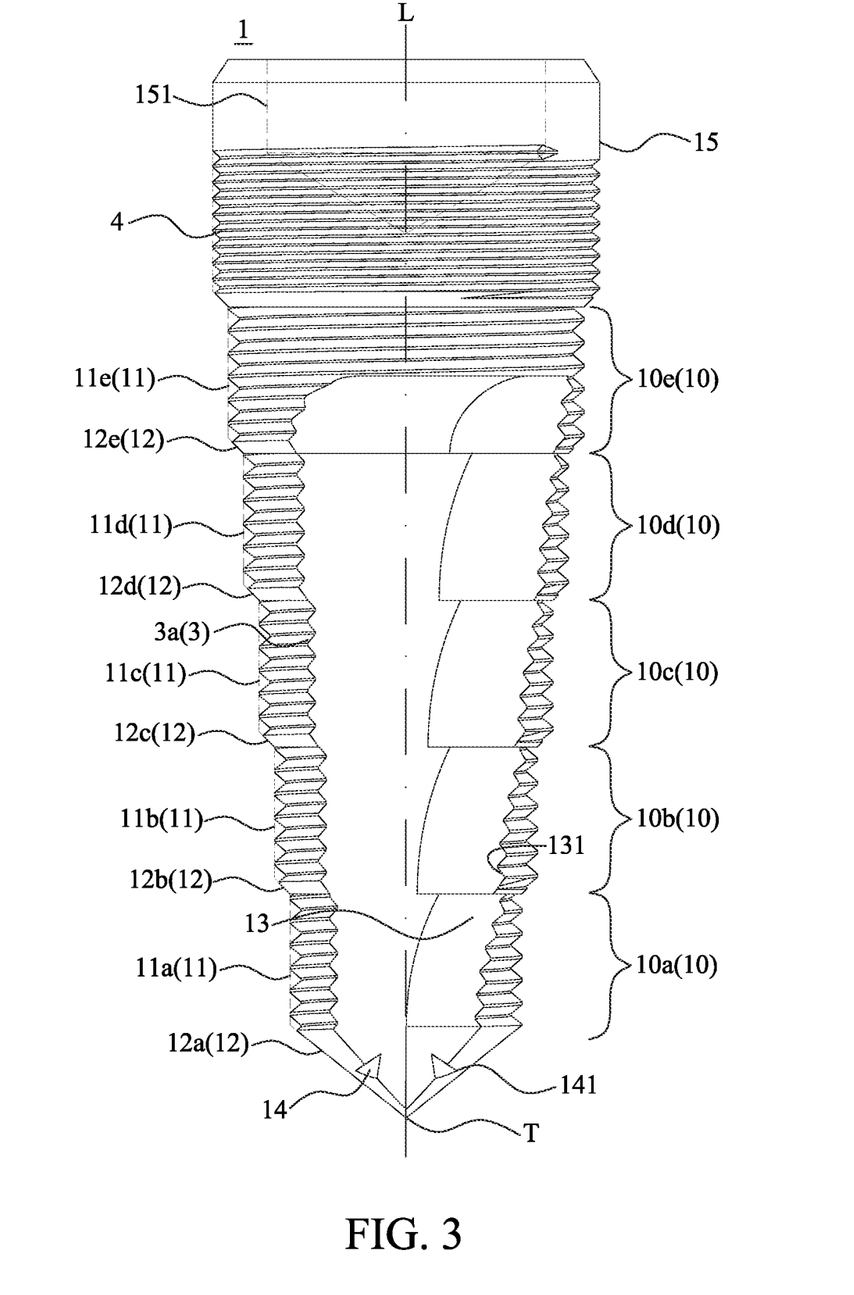
FIG. 3 is a longitudinal sectional view of the orthopedic implant of FIG. 1.

Please refer to FIGS. 1 to 3. An orthopedic implant according to a first embodiment of the present invention includes a main body 1, an external thread 2, and a plurality of lateral cutting flutes 3. The main body 1 is formed with a plurality of steps 10 of different diametrical sizes arranged along a drilling axis L from bottom to top. As shown in FIG. 1, the main body 1 includes a first step 10a, a second step 10b, a third step 10c, a fourth step 10d and a fifth step 10e. However, it is understood the illustrated embodiment is non-restrictive. For example, the orthopedic implant of the present invention may be differently designed to include fewer steps, such as only two steps, or more steps, such as seven steps. The number of the steps 10 can be determined according to the position on a patient's body at where the orthopedic implant is to be used.

Each of the steps 10 includes a cylindrical section 11 and a conical section 12 that provides a drilling surface. More specifically, the first step 10a includes a first cylindrical section 11a having a first diameter, the second step 10b includes a second cylindrical section 11b having a second diameter, the third step 10c includes a third cylindrical section 11c having a third diameter, the fourth step 10d includes a fourth cylindrical section 11d having a fourth diameter, and the fifth step 10e includes a fifth cylindrical section 11e having a fifth diameter. This design gives the main body 1 a downward tapered stepped configuration.

The first step 10a includes a first conical section 12a, which is downward extended and converged on the drilling axis L to form an apex T: the second step 10b includes a second conical section 12b, which is located between the first cylindrical section 11a and the second cylindrical section 11b; the third step 10c includes a third conical section 12c, which is located between the second cylindrical section 11b and the third cylindrical section 11c; the fourth step 10d includes a fourth conical section 12d, which is located between the third cylindrical section 11c and the fourth cylindrical section 11d; and the fifth step 10e includes a fifth conical section 12e, which is located between the fourth cylindrical section 11d and the fifth cylindrical section 11e.

An angle of the apex T is an important parameter in designing the orthopedic implant. The angular design of the apex T determines whether the orthopedic implant is able to drill a bone in a stable state and has a significant influence on the reaction force exerted by the bone on the orthopedic implant during bone drilling and on the cutting energy of the orthopedic implant. The angle of the apex T can be ranged from 70 degrees to 120 degrees. Preferably, the angle of the apex T is ranged from 90 to 120 degrees. In the optimal design, the angle of the apex T is ranged from 70 to 80 degrees.

The external thread 2 is integrally formed on an outer surface of the main body 1. As shown, the external thread 2 is divided into several parts, which are separately located around the first, the second, the third, the fourth and the fifth cylindrical section 11a, 11b, 11c, 11d, 11e. That is, all the cylindrical sections 11 of the main body 1 are covered by the external thread 2, while all the conical sections 12 of the main body 1 are exposed to an outer environment without being covered by the external thread 2. This design allows the first, the second, the third, the fourth and the fifth conical section 12a, 12b, 12c, 12d, 12e to respectively form a drilling surface in different stages of the drilling process.

Figure 5:
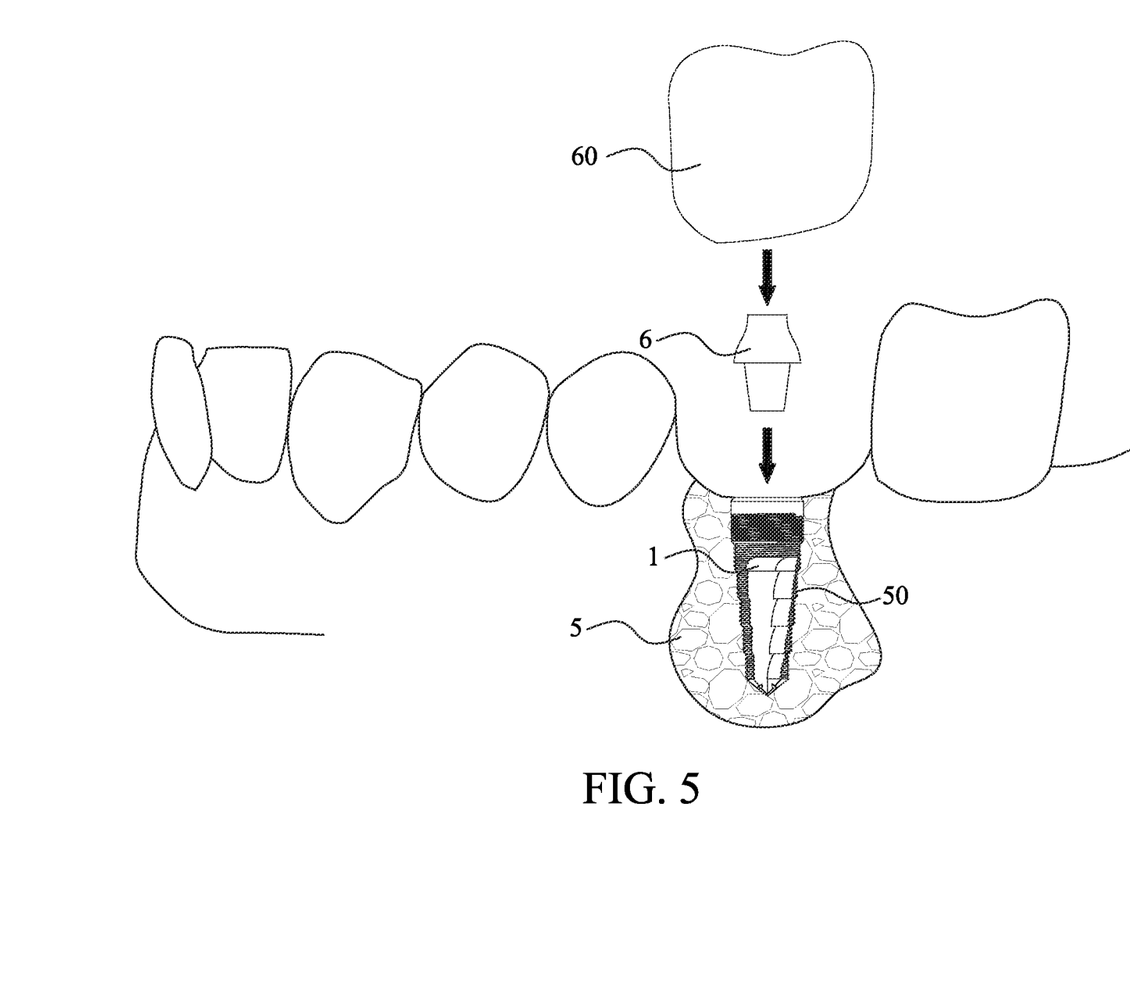
FIG. 5 shows an example of applying the orthopedic implant of the present invention in dentistry.

When the orthopedic implant is driven into a piece of bone, the apex T first drills an implant hole 50 into the bone (see FIG. 5). In this procedure, an inner wall surface of the implant hole 50 is in frictional contact with the first cylindrical section 11a, resulting in accumulation of heat energy thereon. Then, the inner wall surface of the implant hole 50 with accumulated heat energy is cut away by the second conical section 12b of the second step 10b. Thereafter, the inner wall surface of the implant hole 50 is further cut away by conical sections 12 of the third, the fourth and the fifth steps 10c, 10d, 10e sequentially in the same manner. In this way, the main body 1 can be quickly and linearly driven into the bone along the drilling axis L to minimize the situation of tissue necrosis due to overheated bone in around the implant hole 50.

Figure 4:
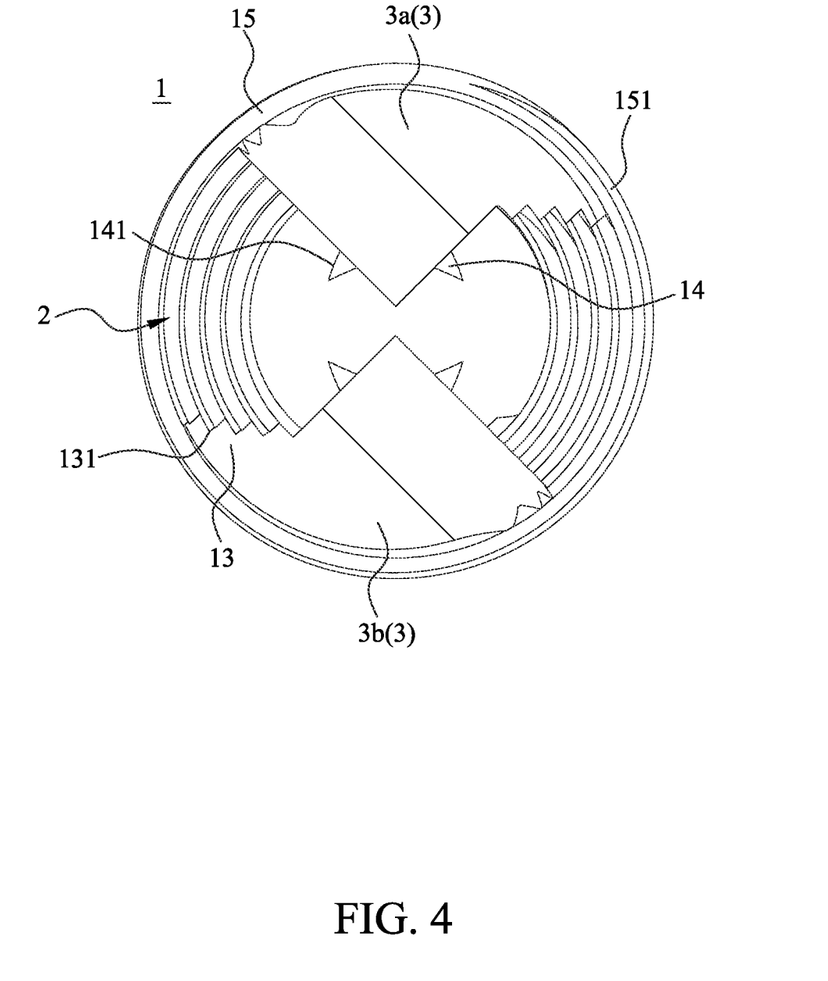
FIG. 4 is a bottom view of the orthopedic implant of FIG. 1.

Please refer to FIGS. 3 and 4. According to a preferred embodiment, the orthopedic implant of the present invention includes a first lateral cutting flute 3a and a second lateral cutting flute 3b extended in the direction of the drilling axis L and symmetrically located at two diametrically opposite sides of the orthopedic implant. The first and the second lateral cutting flute 3a, 3b are mainly used to deliver and fill bone debris in the implant hole 50, so that the orthopedic implant can be firmly held in the implant hole 50 after osseointegration. Meanwhile, extra bone debris can also be washed out of the implant hole 50 via the first and the second lateral cutting flute 3a, 3b to release the bone from stress.

It is understood the illustration of two lateral cutting flutes 3 is only to facilitate easy description of the present invention. In other embodiments, the orthopedic implant may also have three lateral cutting flutes 3 provided thereon, namely, a first lateral cutting flute 3a, a second lateral cutting flute 3b, and a third lateral cutting flute (not shown). In the first embodiment of the present invention, since the first lateral cutting flute 3a and the second lateral cutting flute 3b is identical in structure, only the first lateral cutting flute 3a is described below.

The first lateral cutting flute 3a is sunken from an outer circumferential edge of the external thread 2 into the main body 1, and is extended from the apex T located at a lower end of the main body 1 to the fifth step 10e located around an upper end of the main body 1, while a spacing distance D is left between an upper end of the first lateral cutting flute 3a and the upper end of the fifth step 10e.

As shown, portions of a lateral wall surface of the first lateral cutting flute 3a corresponding to the cylindrical sections 11a~11e are formed into an oblique recessed section 13 each, such that a width of the first lateral cutting flute 3a at each step 10 is gradually increased from the conical section 12 toward the cylindrical section 11, and each of the cylindrical sections 11 has an obliquely cutting blade edge 131 formed thereat. Each of the obliquely cutting blade edges 131 and the conical section 12 located adjacent thereto together include an angle θ between them. The included angle θ is an acute angle ranged between 45° and 70°, so that the obliquely cutting blade edges 131 have good lateral cutting ability. Meanwhile, a length of the first lateral cutting flute 3a located at the apex T has a width gradually reduced from an end of the apex T located adjacent to the first cylindrical section 11a toward a tip of the apex T.

With the plurality of obliquely cutting blade edges 131 formed in the first lateral cutting flute 3a, the orthopedic implant of the present invention can not only drill hole linearly along the drilling axis L, but also laterally cut areas surrounding the bone to expand the hole drilled into the bone. With this design, the orthopedic implant being wrongly implanted into the bone in a skewed direction can still be adjusted in its drilling angle.

Further, when a large quantity of bone debris created during bone drilling is moved into the first lateral cutting flute 3a, the bone debris will fill up the oblique recessed sections 13 of the orthopedic implant. When the bone debris adhered to the orthopedic implant and the surrounding bone are healed later, the orthopedic implant is supported by the oblique recessed sections 13 to be firmly anchored to and integrated into bone; wherein at least one of the external thread 2 and the lateral cutting flutes 3 is subjected to surface treatment to form a coarse surface.

As mentioned above, a large quantity of bone debris will be created during bone drilling with the orthopedic implant. In the event spaces in the lateral cutting flutes 3 are filled up by the bone debris before the orthopedic implant is fully driven into the bone, the orthopedic implant would be adversely stopped from further drilling into the bone successfully. To overcome this problem, the depth of the first lateral cutting flute 3a on the steps 10 is extended from a pitch circle 21 of the external thread 2 into the main body 1 to a location close to the drilling axis L, so that the first lateral cutting flute 3a and the second lateral cutting flute 3b together form an overall volume on the main body 1, and a ratio of the overall volume to a volume of the main body 1 is from 0.4:1 to 0.6:1.

Please refer to FIG. 4. The obliquely cutting blade edges 131 formed on the steps 10 provide a first lateral cutting design on the orthopedic implant of the present invention. Further, the apex T also has at least one lateral cutting member 14 provided thereon. The at least one lateral cutting member 14 includes a laterally cutting blade edge 141 located adjacent to the lateral cutting flutes 3 to provide a second lateral cutting design on the first conical section 12a of the orthopedic implant of the present invention.

In addition, the main body 1 further includes a sealing section 15, which is upward extended from the fifth step 10e. With the sealing section 15, tissue fluid outside the bone is stopped from contacting with the steps 10 after the orthopedic implant is driven into the bone. The sealing section 15 is provided at a top center thereof with an engagement portion 151, to which a rotary tool (not shown) is correspondingly detachably mounted. When the engagement portion 151 is rotated by the rotary tool, the entire orthopedic implant is brought to rotate about the drilling axis L, enabling the apex T and the drilling surfaces provided by the conical sections 12 to move forward linearly to destruct the bone. The sealing section 15 is provided on an outer circumferential surface with a sealing thread 4, which has a pitch smaller than that of the external thread 2 and has an outmost diameter larger than a step diameter defined by the external thread 2 on a circumferential surface of the fifth step 10e.

Please refer to FIG. 5, which shows the orthopedic implant of the present invention is applied in dentistry to be implanted into an alveolar bone 5. First, connect the engagement portion 151 of the orthopedic implant to a dentist handpiece. Then, align the apex T at the lowermost location of the orthopedic implant with a predetermined implantation position and let the dentist handpiece bring the orthopedic implant to drill linearly and form the implant hole 50 in the alveolar bone 5 until all the steps 10 and the sealing section 15 of the whole orthopedic implant are located in the alveolar bone 5. Finally, an abutment 6 is fixed to the engagement portion 151 to expose from the alveolar bone 5 and an artificial crown is fitted on the abutment 6. Therefore, the orthopedic implant of the present invention can be used in place of the conventional drill bit to quickly drill into the alveolar bone 5, and a proper torsional force can be created between the orthopedic implant and the alveolar bone 5 after the drilling of the alveolar bone 5 is completed.

The orthopedic implant of the present invention can also be used as a fixation element for fixing a bone fracture of, for example, a joined cranium, a facial bone 70, or a limb bone 71. In an orthopedic surgery, the manner of using the orthopedic implant is generally determined according to the bone position and the state of bone fracture.

Figure 6:
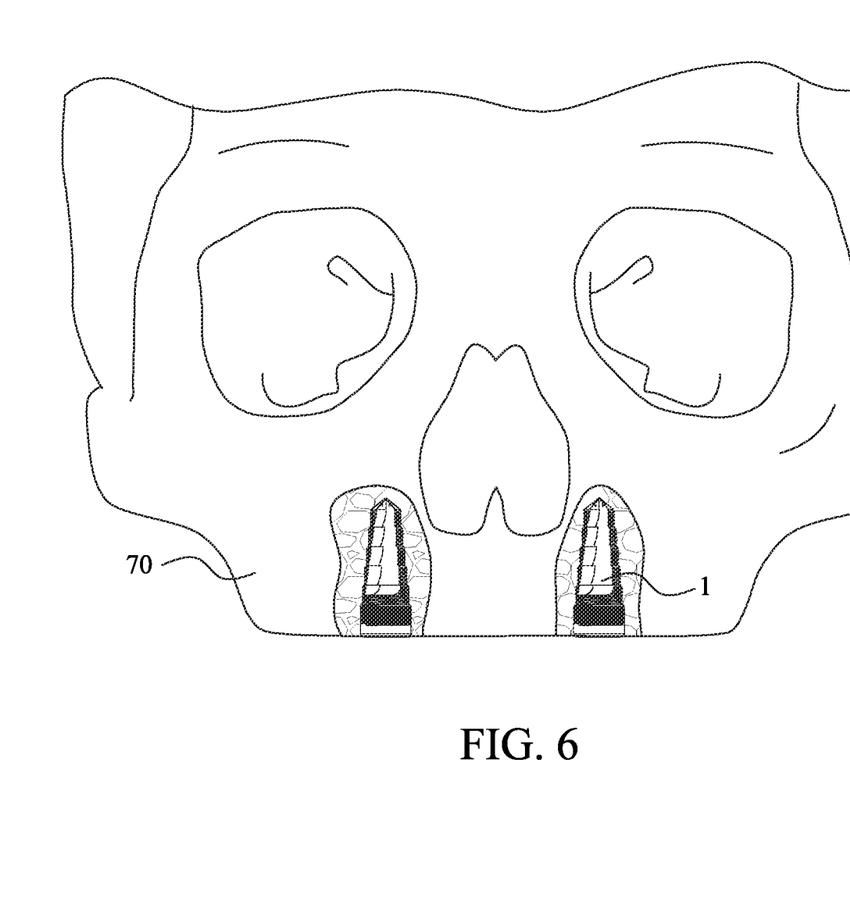
FIG. 6 shows an example of applying the orthopedic implant of the present invention in orthopedics.
Figure 7:
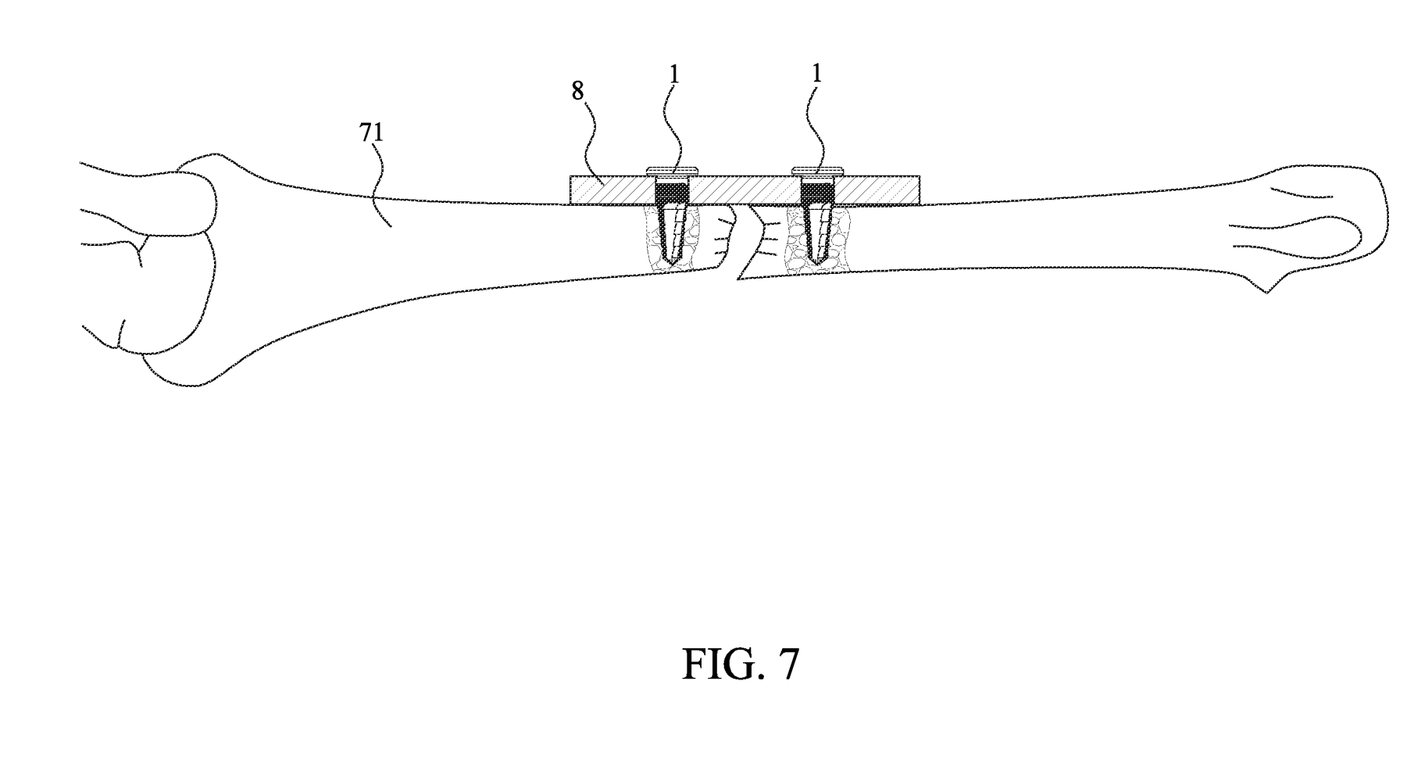
FIG. 7 is a schematic view showing the use of the orthopedic implant of the present invention with a fixation plate in a bone fracture repair surgery.

Please refer to FIG. 6. In the fixation of a fractured facial bone 70, the orthopedic implant alone is fully drilled into the facial bone 70. Please refer to FIG. 7. In the fixation of a fractured limb bone 71, the orthopedic implant can be used along with a bone fixation plate 8 at the position of bone fracture.

The orthopedic implant of the present invention can also be used on human's bones at the spine or pelvis. In addition to the injury caused to the spine or pelvis due to trauma or bone fracture, the most common spine or pelvis disease is the lesion or senile atrophy of the intervertebral discs that results in narrowed intervertebral disc space and accordingly, reduced neural foramen between intervertebral joints to compress the spinal nerve roots to cause paralysis or pain. Aging-related degradation also results in bone loss and hollow-out bone plates in the vertebral body, which causes fractured and collapsed bone.

Generally, in the treatment of the above spine-related conditions, implantation of a spinal fixation plate having one or more windows is necessary. A plurality of the orthopedic implants of the present invention are extended through the fixation plate to attach the latter to two adjacent vertebral segments, so that the fixation plate can stably hold the adjacent vertebral segments in place to relieve the patient's pain due to compressed spinal nerves.

Figure 8:
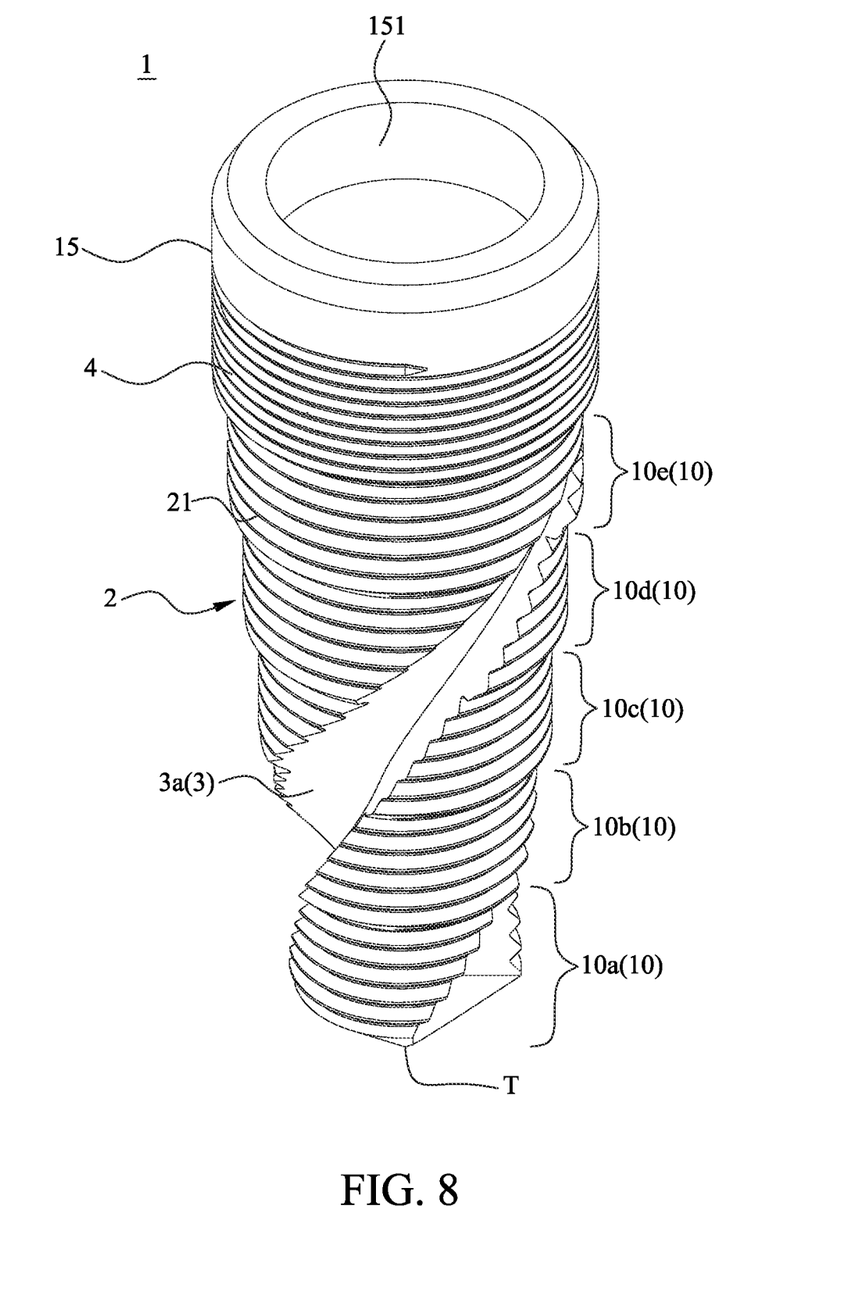
FIG. 8 is a perspective view of an orthopedic implant according to a second embodiment of the present invention.

Lastly, please refer to FIG. 8, in which an orthopedic implant according to a second embodiment of the present invention is shown. Unlike the first embodiment that has straight lateral cutting flutes, the second embodiment includes a first lateral cutting flute 3a and a second lateral cutting flute 3b that are spirally extended from the first step 10a through the second, the third and the fourth step 10b, 10c, 10d to the fifth step 10e; and the first and the second lateral cutting flute 3a, 3b spiral around the steps 10 in the same direction as the external thread 2, so that bone debris created during bone drilling with the orthopedic implant can be successfully guided upward along the first and the second lateral cutting flute 3a, 3b and be discharged out of the implant hole 50.

The present invention has been described with some preferred embodiments thereof and it is understood that many changes and modifications in the described embodiments can be carried out without departing from the scope and the spirit of the invention that is intended to be limited only by the appended claims.

What is claimed is:

1. An orthopedic implant that saves bone cutting with drill bits in advance in orthopedic surgery, comprising:
    a main body being formed with a plurality of steps arranged along a drilling axis and having diametrical sizes gradually increased from bottom to top, so as to have a stepped and downward tapered overall configuration; each of the steps including a cylindrical section and a conical section providing a drilling surface, and the conical section of the step having the smallest diametrical size being downward extended and tapered to form an apex;
    an external thread being formed on an outer surface of the main body to cover all cylindrical sections of the main body, while all conical sections of the main body are exposed to an outer environment without being covered by the external thread; and
    a plurality of lateral cutting flutes being formed on the external thread and sunken into the main body; and each of the lateral cutting flutes being extended from the apex located at a lower end of the main body to the step having the largest diametrical size and located around an upper end of the main body, while a spacing distance is formed between an upper end of the lateral cutting flute and the upper end of the main body;
    wherein the orthopedic implant being rotatable about the drilling axis to drive the apex and all drilling surfaces provided by the conical sections into a piece of bone linearly to destruct the bone; and
    wherein a length of each of the lateral cutting flutes corresponding to the apex has a width that is gradually reduced from an end of the apex located adjacent to the cylindrical section of a diametrically smallest step toward a tip of the apex.

2. The orthopedic implant as claimed in claim 1, wherein a side of each of the lateral cutting flutes is formed a plurality of oblique recessed portions corresponding to the cylindrical sections, such that each of the cylindrical sections has an obliquely cutting blade edge; and an acute angle is formed between the obliquely cutting blade edge and the conical section located at the same step.

3. The orthopedic implant as claimed in claim 2, further comprising a plurality of lateral cutting members formed on the apex, and each of the lateral cutting members having a laterally cutting blade edge correspondingly located adjacent to one of the lateral cutting flutes.

4. The orthopedic implant as claimed in claim 1, further comprising a plurality of lateral cutting members formed on the apex, and each of the lateral cutting members having a laterally cutting blade edge correspondingly located adjacent to one of the lateral cutting flutes.

5. The orthopedic implant as claimed in claim 1, wherein a length of each of the lateral cutting flutes corresponding to each of the steps has a width that is gradually increased from the bottom toward the top of said each step.

6. The orthopedic implant as claimed in claim 1, wherein at least one of the external thread and the lateral cutting flutes is subjected to surface treatment to form a coarse surface.

7. The orthopedic implant as claimed in claim 1, wherein the main body further includes a sealing section located adjacent to a diametrically largest step; and the sealing section being provided on an outer circumferential surface with a sealing thread, the sealing thread has an outmost diameter larger than a step diameter defined by the external thread on a circumferential surface of the diametrically largest step.

8. The orthopedic implant as claimed in claim 7, wherein the sealing section is provided at a top center with an engagement portion, and a rotary tool is correspondingly detachably mounted to the engagement portion for driving the whole orthopedic implant into the bone; and an abutment being fixedly connectable to the engagement portion to expose from an alveolar bone when the orthopedic implant is applied in dentistry.

9. The orthopedic implant as claimed in claim 1, wherein a depth of the lateral cutting flutes on the steps starts from a pitch circle of the external thread to extend into the main body to a location close to the drilling axis, such that a ratio of an overall volume of all the lateral cutting flutes on the main body to a volume of the main body is ranged between 0.45:1 and 0.55:1.

* * * * *